(12) United States Patent
King et al.

(10) Patent No.: US 9,717,925 B2
(45) Date of Patent: Aug. 1, 2017

(54) MOTION ACTUATED AED COMMUNICATOR

(71) Applicant: KONINKLIJKE PHILIPS N.V., Eindhoven (NL)

(72) Inventors: Marty King, Bothell, WA (US); Catherine Ann Thompson, Seattle, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/030,266

(22) PCT Filed: Oct. 21, 2014

(86) PCT No.: PCT/IB2014/065489
§ 371 (c)(1),
(2) Date: Apr. 18, 2016

(87) PCT Pub. No.: WO2015/063650
PCT Pub. Date: May 7, 2015

(65) Prior Publication Data
US 2016/0250492 A1    Sep. 1, 2016

Related U.S. Application Data

(60) Provisional application No. 61/898,654, filed on Nov. 1, 2013.

(51) Int. Cl.
*A61N 1/00* (2006.01)
*A61N 1/39* (2006.01)
(Continued)

(52) U.S. Cl.
CPC ......... *A61N 1/3993* (2013.01); *A61N 1/3987* (2013.01); *H04M 1/72538* (2013.01); *H04W 4/22* (2013.01); *H04W 64/00* (2013.01)

(58) Field of Classification Search
CPC ...... A61N 1/39; A61N 1/3968; A61N 1/3993; A61N 1/3987; H04M 1/72538; H04W 4/22; H04W 64/00
See application file for complete search history.

(56) References Cited

U.S. PATENT DOCUMENTS 4,696,653 A    9/1987   McKeefery
5,971,921 A    10/1999  Timbel
(Continued)

FOREIGN PATENT DOCUMENTS

JP    2006512156 A    4/2006
JP    2012164670 A    8/2012
(Continued)

*Primary Examiner* — Mallika D Fairchild

(57) ABSTRACT

A motion sensitive communicator (40) employs an assembly of a wireless phone (41), a motion sensor (44) and a battery (45). In operation, the motion sensor (44) power couples the battery (45) to the wireless phone (41) responsive to a sensing of any movement of a portable defibrillator (20) supporting the communicator (40). A power coupling of the battery (45) to the wireless phone (41) automatically activates the wireless phone (41) to register to a wireless network, and an activation of the wireless phone (41) enables the wireless phone (41) to execute a call to an emergency service center over the wireless network responsive to a manual actuation of the wireless phone (41). The battery (45) is power decoupled from the wireless phone (41) responsive to an absence of a call from the wireless phone (41) to the emergency service center within a time period initiated by a power coupling of the battery (45) to the wireless phone (41).

13 Claims, 2 Drawing Sheets

(51) Int. Cl.
*H04M 1/725* (2006.01)
*H04W 4/22* (2009.01)
*H04W 64/00* (2009.01)

(56) References Cited

U.S. PATENT DOCUMENTS

| | | | |
|---|---|---|---|
| 6,975,941 B1 * | 12/2005 | Lau | G01C 21/00 340/539.13 |
| 7,289,029 B2 | 10/2007 | Medema et al. | |
| 2006/0152934 A1 | 7/2006 | Lavergne | |
| 2011/0060378 A1 * | 3/2011 | Tuysserkani | A61B 5/0022 607/5 |
| 2011/0291017 A1 | 12/2011 | Frach | |
| 2012/0207053 A1 | 8/2012 | Zhao | |
| 2013/0012151 A1 | 1/2013 | Hankins | |

FOREIGN PATENT DOCUMENTS

| | | |
|---|---|---|
| WO | 0152934 A1 | 7/2001 |
| WO | 03013177 A1 | 2/2003 |
| WO | 2011029101 A1 | 3/2011 |

\* cited by examiner

MOTION ACTUATED AED COMMUNICATOR

CROSS-REFERENCE TO PRIOR APPLICATIONS

This application is the U.S. National Phase application under 35 U.S.C. §371 of International Application No. PCT/IB2014/065489, filed on Oct. 21, 2014, which claims the benefit of U.S. Provisional Patent Application No. 61/898,654, filed on Nov. 1, 2013. These applications are hereby incorporated by reference herein.

The present invention generally relates to automatic external defibrillators ("AED"). The present invention specifically relates to an actuation of a portable AED communicator for executing a call to an emergency service center.

As known in the art, a communicator of a portable AED employs a rescue button for a wireless call by an operator of the AED to an emergency service center during an application by the operator of the AED to a patient experiencing sudden cardiac arrest or another critical life-saving event. This wireless call enables a trained professional at the emergency service center to provide verbal assistance to the operator of the AED and to further contact emergency services as needed. However, the communicator has two (2) conflicting requirements.

Specifically, the first requirement of the communicator is an immediate wireless call to the emergency service center upon actuation in view of each second possibly making a difference to a heartbeat recovery of the patient via the AED. The second requirement of the communicator is to prevent any unnecessary drain on its battery (e.g. internal battery or external power supply), particularly when the portable AED is not being operated on behalf of a patient (e.g., the portable AED is shelved). The conflict between these two (2) requirements of the communicator derives from the time period necessary for the communicator to power up when turned on from a powered down state to save battery life and upon being powered up, to find and successfully register on a wireless network (e.g., a cellular network) associated with the emergency service center. Under current wireless technology, this time period may be in excess of thirty (30) seconds, which is an unacceptably long time for a patient experiencing sudden cardiac arrest or another critical life-saving event.

The present invention addresses the conflicting requirements of the communicator by providing a motion sensitive communicator that minimizes a time for connecting an operator of the AED to the emergency service center while maximizing a life of the battery of the communicator (e.g., at least four (4) years).

One form of the present invention is a motion sensitive communicator employing an assembly of a wireless phone, a motion sensor and a battery. In operation, the motion sensor power couples the battery to the wireless phone responsive to a sensing of any movement of a portable defibrillator supporting the communicator. A power coupling of the battery to the wireless phone (e.g., a cellular phone) automatically activates the wireless phone to register to a wireless network (e.g., cellular network), and an activation of the wireless phone enables the wireless phone to execute a call to an emergency service center over the wireless network responsive to a manual actuation of the wireless phone.

By further operation, the battery is power decoupled from the wireless phone responsive to an absence of a call from the wireless phone to the emergency service center within a time period initiated by a power coupling of the battery to the wireless phone.

A second form of the present invention is a defibrillation device employing the portable defibrillator enclosed within a housing supporting the aforementioned motion sensitive communicator (e.g., the communicator mounted to or slotted within the housing).

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

To facilitate an understanding of the present invention, exemplary embodiments of the present invention will be provided herein directed to a communicator association with a portable defibrillator movable by any variety of modes including, but not limited to, a hand-held movement or a translational movement via wheels or the like.

Figure 1:
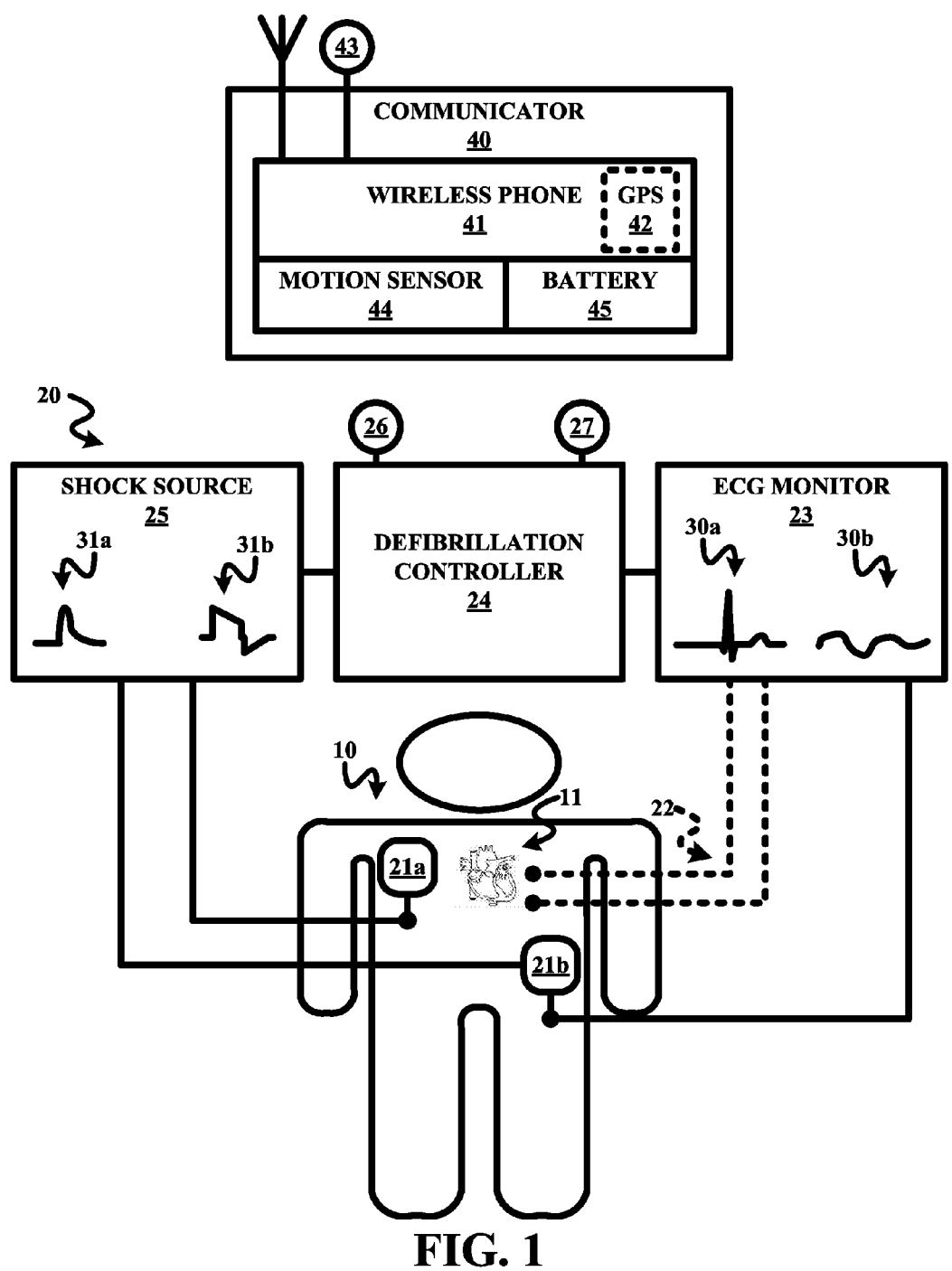
FIG. 1 illustrates an exemplary embodiment of a defibrillator and a communicator in accordance with the present invention.

Referring to FIG. 1, a portable defibrillator 20 of the present invention employs a pair of electrode pads or paddles 21, optional ECG leads 22, a ECG monitor 23 (internal or external), a defibrillation controller 24, and a shock source 25.

Electrode pads/paddles 21 are structurally configured as known in the art to be conductively applied to a patient 10 in an anterior-apex arrangement as shown in FIG. 1 or in an anterior-posterior arrangement (not shown). Electrode pad/paddles 21 conduct a defibrillation shock from shock source 25 to a heart 11 of patient 10 and conduct an ECG signal (not shown) representative of electrical activity of heart 11 of patient 10 to ECG monitor 23. Alternatively or concurrently, ECG leads 22 are connected to patient 10 as known in the art to conduct the ECG signal to ECG monitor 23.

ECG monitor 23 is structurally configured as known in the art for processing the ECG signal to measure the electrical activity of heart 11 of patient 10 as an indication patient 10 is experiencing an organized heartbeat condition or an unorganized heartbeat condition. An example of the ECG signal indicating an organized heartbeat condition is an ECG waveform 30a that is representative of an organized contraction of the ventricles of heart 11 of patient 10 being capable of pumping blood. An example of the ECG signal indicating an unorganized heartbeat condition is an ECG waveform 30b that is representative of a ventricular fibrillation of heart 11 of patient 10.

Shock source 25 is structurally configured as known in the art to store electric energy for delivery of a defibrillation shock 31 via electrode pads/paddles 21 to heart 11 of patient 10 as controlled by defibrillation controller 24. In practice, defibrillation shock 31 may have any waveform as known in the art. Examples of such waveforms include, but are not limited to, a monophasic sinusoidal waveform (positive sine wave) 31a and a biphasic truncated waveform 31b as shown in FIG. 1.

In one embodiment, shock source 25 employs a high voltage capacitor bank (not shown) for storing a high voltage via a high voltage charger and a power supply upon a pressing of a charge button 26. Shock source 25 further employs a switching/isolation circuit (not shown) for selectively applying a specific waveform of an electric energy charge from the high voltage capacitor bank to electrode pads/paddles 21 as controlled by defibrillation controller 24.

Defibrillation controller 24 is structurally configured as known in the art to execute a manual cardioversion via a shock button 27 and/or an automatic cardioversion. In practice, defibrillation controller 24 employs hardware/circuitry (e.g., processor(s), memory, etc.) for executing a manual and/or an automatic cardioversion installed as software/firmware within defibrillation controller 24.

Still referring to FIG. 1, a motion sensitive communicator 40 of the present invention employs a wireless phone 41, a motion sensor 44 and an internal battery 45.

Wireless phone 41 is structurally configured as known in the art to be automatically activated upon a connection to battery 45 and to execute a phone call over a wireless network to a specified destination upon a manual actuation of wireless phone 41 via a phone actuator 43 (e.g., a rescue button). In practice, wireless phone 41 may include a global location capability (e.g., GPS module 42). In one embodiment, wireless phone 41 is a cellular phone capable of executing a phone call over a cellular network to a specified destination upon a manual actuation of the cellular phone via a call button.

Motion sensor 44 is structurally configured as known in the art to detect any motion of an object relative to the surface of the earth. In one embodiment, motion sensor 44 is an accelerometer.

Battery 45 is structurally configured as known in the art for powering an electronic device (e.g., wireless phone 41) connected to battery 45. In one embodiment, battery 45 is a non-rechargeable primary battery of lithium-manganese chemistry. Another embodiment of battery 45 is a rechargeable battery. Yet another embodiment of the battery 45 is a the defibrillator battery power supply itself, and so is a shared power supply with portable defibrillator 20.

Figure 2:
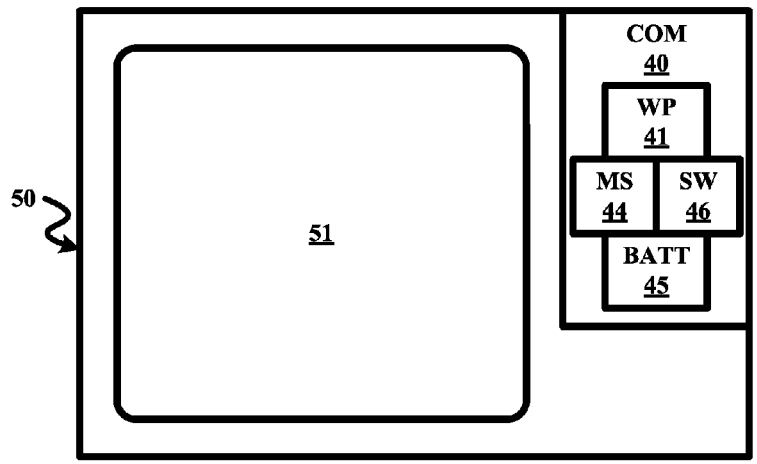
FIG. 2 illustrates an exemplary embodiment of a defibrillator housing supporting the communicator of FIG. 1 in accordance with the present invention.

For purposes of the present invention, motion sensor 44 is further structurally configured to power couple battery 45 to wireless phone 41 in response to a detection by motion sensor 44 of any movement of portable defibrillator 20. In one embodiment, as shown in FIG. 2, portable defibrillator 20 (not shown) is enclosed by a housing 50 having a display screen 51. Communicator 40 is supported by housing 50 by any variety of known modes including, but not limited to, a mounting of communicator 40 to housing 50 as shown in FIG. 2 or a placement of communicator 40 within a slot of housing 50. The support of communicator 40 by housing 50 facilitates detection by motion sensor 44 of any movement of portable defibrillator 20.

In practice, a power coupling of battery 45 to wireless phone 41 may be executed in a variety of modes. In one embodiment as shown in FIG. 2, communicator 40 employs a switch ("SW") 46 controllable by motion sensor ("MS") 44 to power couple battery ("BAT") 45 to wireless phone ("WP") 41 and controllable by wireless phone 41 to power decouple battery 45 from wireless phone 41.

Figure 3:
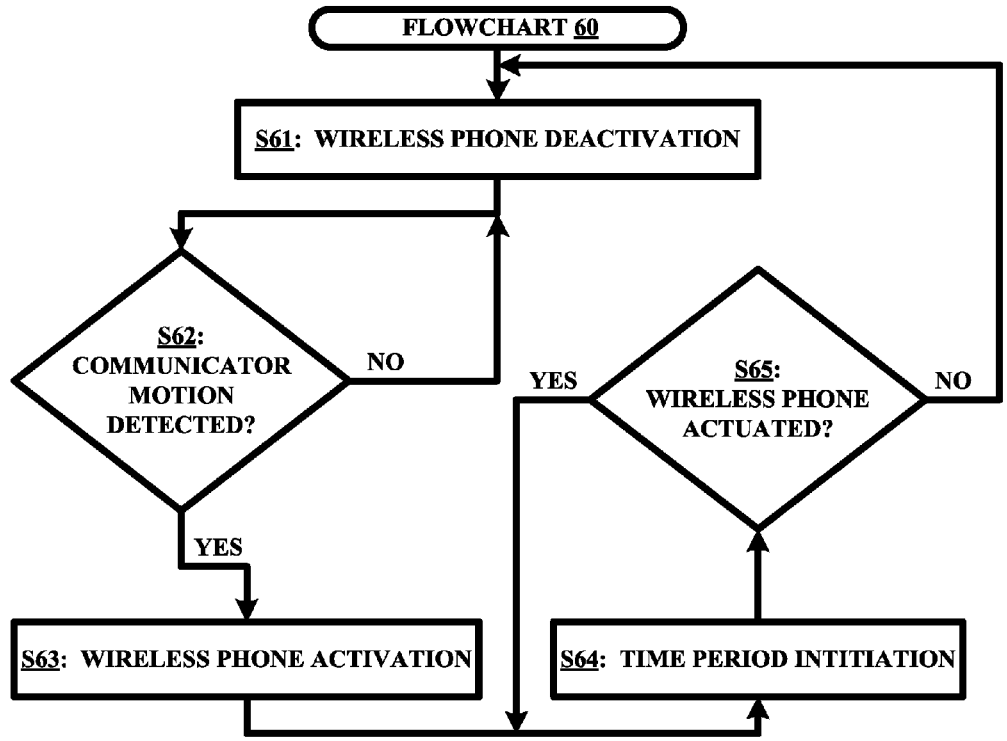
FIG. 3 illustrates a flow chart representative of an exemplary communicator power-on connection method in accordance with the present invention.

FIG. 3 illustrates a flowchart 60 representative of an operational method of communicator 40 as shown in FIG. 2.

Specifically, a stage S61 of flowchart 60 encompasses an initial deactivation of wireless phone 41 by a power decoupling of battery 45 from wireless phone 41 via an opening of switch 46.

A stage S62 of flowchart 60 encompasses motion sensor 44 continually monitoring communicator 40 for any movement of portable defibrillator 20 via motion of housing 50.

Upon motion sensor 44 sensing movement of portable defibrillator 20, a stage S63 of flowchart 60 encompasses an automatic activation of wireless phone 41 to register to a wireless network (not shown in FIG. 2) by a power coupling of battery 45 to wireless phone 41 via a closing of switch 46, and a stage S64 of flowchart encompasses wireless phone 41 initiating a time period for executing a call to an emergency service center (not shown in FIG. 2).

A stage S65 of flowchart 60 is designed to test whether wireless phone 41 was actuated within a current time period to call an emergency service center. If wireless phone 41 is actuated during a current time period, then stage S65 encompasses wireless phone 41 returning to stage S64 for reinitializing the time period upon a termination of the call by wireless phone 41 to the emergency service center. If wireless phone 41 is not actuated during a current time period, then stage S65 encompasses a return to stage S61 for deactivating wireless phone 41 by a power decoupling of battery 45 from wireless phone 41 via a re-closing of switch 46.

Flowchart 60 will consistently proceed through stages S61-S65 accordingly whereby battery 45 will be power coupled/decoupled to/from wireless phone 41 in a manner designed to minimize a time for connecting an operator of portable defibrillator 20 to the emergency service center while maximizing a life of battery 45 (e.g., at least four (4) years).

While various embodiments of the present invention have been illustrated and described, it will be understood by those skilled in the art that the embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. A motion sensitive communicator adapted to be supported by a housing of a portable defibrillator, the motion sensitive communicator comprising:
   an assembly of a wireless phone, a motion sensor and a battery,
      wherein the motion sensor is operable to power couple the battery to the wireless phone responsive to the motion sensor sensing of any movement, relative to a surface of the earth, of the portable defibrillator in which the motion sensitive communicator is supported by the housing of the portable defibrillator,
      wherein responsive to a power coupling of the battery to the wireless phone, the wireless phone automatically activates the wireless phone to register to a wireless network, and
      wherein responsive to an activation of the wireless phone, via the power coupling of the battery to the wireless phone, the wireless phone is configured to (i) execute a call to an emergency service center over the wireless network in response to a manual actuation via a phone actuator or rescue button of the wireless phone for executing the call to the emergency service center, and (ii) not execute the call to the emergency service center in response to no manual actuation via the phone actuator or rescue button of the wireless phone, and further wherein the wireless phone is configured (i) to initiate a time period in response to the power coupling of the battery to the wireless phone and (ii) to power decouple the batter from the wireless phone in response to an absence of the manual actuation via the phone actuator or rescue button of the wireless phone for executing the call from the wireless phone to the emergency service center within the time period.

2. The motion sensitive communicator of claim 1, wherein the motion sensor includes an accelerometer.

3. The motion sensitive communicator of claim 1, further comprising:
a switch operable by the motion sensor to connect the battery to the wireless phone for power coupling the battery to the wireless phone.

4. The motion sensitive communicator of claim 1, wherein the wireless phone is a cellular phone, and wherein the wireless network is a cellular network.

5. The motion sensitive communicator of claim 1, wherein the wireless phone is operable to detect a global location of the motion sensitive communicator.

6. A defibrillation device, comprising:
a portable defibrillator enclosed within a housing; and
a motion sensitive communicator supported by the housing, the motion sensitive communicator including an assembly of a wireless phone, a motion sensor and a battery,
  wherein the motion sensor is operable to power couple the battery to the wireless phone responsive to the motion sensor sensing of any movement, relative to a surface of the earth, of the portable defibrillator in which the motion sensitive communicator is supported by the housing of the portable defibrillator,
  wherein responsive to a power coupling of the battery to the wireless phone, the wireless phone automatically activates the wireless phone to register to a wireless network, and
  wherein responsive to an activation of the wireless phone, via the power coupling of the battery to the wireless phone, the wireless phone is configured to (i) execute a call to an emergency service center over the wireless network in response to a manual actuation via a phone actuator or rescue button of the wireless phone for executing the call to the emergency service center, and (ii) not execute the call to the emergency service center in response to no manual actuation via the phone actuator or rescue button of the wireless phone,
  and further wherein the wireless phone is configured (i) to initiate a time period in response to the power coupling of the battery to the wireless phone and (ii) to power decouple the battery from the wireless phone in response to an absence of the manual actuation via the phone actuator or rescue button of the wireless phone for executing the call from the wireless phone to the emergency service center within the time period.

7. The defibrillation device of claim 6, wherein the motion sensor includes an accelerometer.

8. The defibrillation device of claim 6, wherein motion sensitive communicator further includes a switch operable by the motion sensor to selectively connect the battery to the wireless phone for power coupling the battery to the wireless phone.

9. The defibrillation device of claim 6,
wherein the wireless phone is a cellular phone, and
wherein the wireless network is a cellular network.

10. The defibrillation device of claim 6, wherein the wireless phone is operable to detect a global location of the motion sensitive communicator.

11. The defibrillation device of claim 6, wherein the portable defibrillator includes an electrocardiogram monitor operable to measure electrical activity of a heartbeat of a patient.

12. The defibrillation device of claim 6, wherein the portable defibrillator includes a defibrillation controller operable to control a delivery of electric energy to a heart of a patient responsive to a measurement of the electrical activity of a heartbeat of the patient.

13. The defibrillation device of claim 6, wherein the portable defibrillator includes a shock source operable to deliver electric energy to a heart of a patient.

\* \* \* \* \*